(12) United States Patent
Fry et al.

(10) Patent No.: US 9,974,602 B2
(45) Date of Patent: May 22, 2018

(54) SURGICAL INSTRUMENTS AND DEVICES AND METHODS FACILITATING THE MANUFACTURE OF THE SAME

(71) Applicant: COVIDIEN LP, Mansfield, MA (US)

(72) Inventors: Monte S. Fry, Longmont, CO (US); Stephen J. Stamm, Wheat Ridge, CO (US)

(73) Assignee: COVIDIEN LP, Mansfield, MA (US)

( * ) Notice: Subject to any disclaimer, the term of this patent is extended or adjusted under 35 U.S.C. 154(b) by 293 days.

(21) Appl. No.: 14/722,859

(22) Filed: May 27, 2015

(65) Prior Publication Data

US 2016/0345993 A1 Dec. 1, 2016

(51) Int. Cl.
*A61B 18/14* (2006.01)
*A61B 17/29* (2006.01)
(Continued)

(52) U.S. Cl.
CPC .......... *A61B 18/1445* (2013.01); *A61B 17/29* (2013.01); *A61B 2017/00526* (2013.01);
(Continued)

(58) Field of Classification Search
CPC .......... B25B 27/04; B25B 27/08; B25G 3/26; Y10T 29/537; Y10T 29/53809;
(Continued)

(56) References Cited

U.S. PATENT DOCUMENTS

| 162,643 | A | * | 4/1875 | Goddu | .......... F16B 15/08 411/445 |
| 176,295 | A | * | 4/1876 | Goddu | .......... F16B 15/08 411/445 |

(Continued)

FOREIGN PATENT DOCUMENTS

| CN | 201299462 | 9/2009 |
| DE | 2415263 A1 | 10/1975 |

(Continued)

OTHER PUBLICATIONS

U.S. Appl. No. 14/098,953, filed Dec. 6, 2013; inventor: Cunningham.

(Continued)

*Primary Examiner* — Jason L Vaughan

(57) ABSTRACT

An assembly tool for facilitating assembly of a surgical instrument includes a handle, a neck extending from the handle, and a portion of or an entire pivot pin engaged with the neck via a frangible connection. The pivot pin is engagable with the surgical instrument. The frangible connection is configured to break upon application of stress thereto above a threshold, thereby separating the pivot pin (or portion thereof) from the neck. A method of assembling using such an assembly tool includes positioning a component of a surgical instrument for receipt of a pivot pin, manipulating the assembly tool to operably engage the pivot pin with the component, and manipulating the assembly tool to apply stress to the frangible connection to break-off the pivot pin (or portion thereof) from the assembly tool along the frangible connection.

4 Claims, 7 Drawing Sheets

(51) Int. Cl.
| | |
|---|---|
| B25G 3/26 | (2006.01) |
| B25B 27/08 | (2006.01) |
| B25B 27/04 | (2006.01) |
| A61B 17/00 | (2006.01) |
| A61B 90/00 | (2016.01) |

(52) U.S. Cl.
CPC . *A61B 2017/2947* (2013.01); *A61B 2090/037* (2016.02); *B25B 27/04* (2013.01); *B25B 27/08* (2013.01); *B25G 3/26* (2013.01); *Y10T 29/537* (2015.01); *Y10T 29/53809* (2015.01); *Y10T 29/53909* (2015.01); *Y10T 29/53943* (2015.01); *Y10T 29/53987* (2015.01)

(58) Field of Classification Search
CPC ......... Y10T 29/53909; Y10T 29/53943; Y10T 29/53987; Y10T 29/54
USPC .... 81/44; 411/2, 3, 4, 5, 442, 443, 444, 445
See application file for complete search history.

(56) References Cited

U.S. PATENT DOCUMENTS

| | | | | |
|---|---|---|---|---|
| 182,495 | A * | 9/1876 | Trask | F16B 15/08 411/445 |
| 519,553 | A * | 5/1894 | Rounds | E04G 23/0203 206/820 |
| 829,587 | A * | 8/1906 | Jones | B25C 5/0242 227/107 |
| 1,677,269 | A * | 7/1928 | Burghart | F16B 12/30 411/5 |
| 1,696,523 | A * | 12/1928 | Cochran | F16B 39/282 411/5 |
| 2,247,499 | A * | 7/1941 | Hutchison, Jr. | B25B 13/065 206/338 |
| 2,279,401 | A * | 4/1942 | Hutchison, Jr. | B25B 13/065 470/164 |
| 2,286,809 | A * | 6/1942 | Hutchison, Jr. | B25B 23/065 29/240 |
| 2,289,785 | A * | 7/1942 | Hutchison, Jr. | B25B 13/065 206/338 |
| 2,366,510 | A * | 1/1945 | Frank | F16B 19/06 206/343 |
| 2,619,965 | A | 12/1952 | Goldstone | |
| 2,674,736 | A * | 4/1954 | Chalmer | B25C 3/002 227/126 |
| 2,704,399 | A | 3/1955 | Melcher | |
| 2,948,056 | A * | 8/1960 | Muenchinger | B25B 23/065 206/338 |
| 3,040,425 | A * | 6/1962 | Muenchinger | B25B 23/065 29/240 |
| 3,302,648 | A | 2/1967 | Nelson | |
| 3,434,209 | A * | 3/1969 | Weissman | A61C 5/35 433/225 |
| 3,498,174 | A * | 3/1970 | Hatter | F16B 31/021 411/5 |
| 3,528,466 | A * | 9/1970 | Tracy | B25B 23/065 206/338 |
| 3,675,328 | A * | 7/1972 | Weissman | A61O 5/35 433/225 |
| 3,861,043 | A * | 1/1975 | Lieb | A61C 5/35 433/225 |
| 4,053,982 | A * | 10/1977 | Weissman | A61O 5/35 411/2 |
| 4,083,101 | A * | 4/1978 | Coller | H01R 43/22 29/278 |
| D249,549 | S | 9/1978 | Pike | |
| 4,189,834 | A * | 2/1980 | Smith | A61O 5/35 433/225 |
| 4,202,101 | A * | 5/1980 | Weissman | A61O 5/35 433/225 |
| 4,205,444 | A * | 6/1980 | Weissman | A61O 5/35 433/128 |
| 4,255,145 | A * | 3/1981 | Weissman | A61C 1/144 433/128 |
| D263,020 | S | 2/1982 | Rau, III | |
| 4,380,433 | A * | 4/1983 | Ellman | A61C 19/00 226/127 |
| 4,397,634 | A * | 8/1983 | Biggs | A61C 5/35 433/225 |
| 4,595,376 | A * | 6/1986 | Nordin | A61O 5/35 226/127 |
| D295,893 | S | 5/1988 | Sharkany et al. | |
| D295,894 | S | 5/1988 | Sharkany et al. | |
| 4,759,715 | A * | 7/1988 | Weissman | A61O 5/35 433/225 |
| D298,353 | S | 11/1988 | Manno | |
| D299,413 | S | 1/1989 | DeCarolis | |
| 4,850,874 | A * | 7/1989 | Weissman | A61O 5/35 433/225 |
| 5,207,545 | A * | 5/1993 | Kochanski | B25B 23/065 206/338 |
| D343,453 | S | 1/1994 | Noda | |
| 5,281,066 | A * | 1/1994 | Fitz | B23P 6/00 411/378 |
| D348,930 | S | 7/1994 | Olson | |
| D349,341 | S | 8/1994 | Lichtman et al. | |
| D354,564 | S | 1/1995 | Medema | |
| 5,395,375 | A | 3/1995 | Turkel et al. | |
| D358,887 | S | 5/1995 | Feinberg | |
| 5,499,892 | A * | 3/1996 | Reed | B23G 5/06 29/402.17 |
| 5,517,723 | A * | 5/1996 | Sircy | G02C 5/2281 16/228 |
| D384,413 | S | 9/1997 | Zlock et al. | |
| H1745 | H | 8/1998 | Paraschac | |
| D402,028 | S | 12/1998 | Grimm et al. | |
| D408,018 | S | 4/1999 | McNaughton | |
| 5,928,236 | A * | 7/1999 | Augagneur | A61B 17/8605 411/405 |
| 5,951,549 | A | 9/1999 | Richardson et al. | |
| 5,971,987 | A * | 10/1999 | Huxel | A61B 17/8605 411/2 |
| D416,089 | S | 11/1999 | Barton et al. | |
| 5,976,132 | A | 11/1999 | Morris | |
| 6,021,694 | A | 2/2000 | Beger | |
| D424,694 | S | 5/2000 | Tetzlaff et al. | |
| D425,201 | S | 5/2000 | Tetzlaff et al. | |
| H1904 | H | 10/2000 | Yates et al. | |
| D449,886 | S | 10/2001 | Tetzlaff et al. | |
| 6,322,561 | B1 | 11/2001 | Eggers et al. | |
| D453,923 | S | 2/2002 | Olson | |
| D454,951 | S | 3/2002 | Bon | |
| D457,958 | S | 5/2002 | Dycus et al. | |
| D457,959 | S | 5/2002 | Tetzlaff et al. | |
| H2037 | H | 7/2002 | Yates et al. | |
| D465,281 | S | 11/2002 | Lang | |
| D466,209 | S | 11/2002 | Bon | |
| D493,888 | S | 8/2004 | Reschke | |
| D496,997 | S | 10/2004 | Dycus et al. | |
| D499,181 | S | 11/2004 | Dycus et al. | |
| D502,994 | S | 3/2005 | Blake, III | |
| D509,297 | S | 9/2005 | Wells | |
| D525,361 | S | 7/2006 | Hushka | |
| D531,311 | S | 10/2006 | Guerra et al. | |
| D533,274 | S | 12/2006 | Visconti et al. | |
| D533,942 | S | 12/2006 | Kerr et al. | |
| D535,027 | S | 1/2007 | James et al. | |
| D538,932 | S | 3/2007 | Malik | |
| D541,418 | S | 4/2007 | Schechter et al. | |
| D541,611 | S | 5/2007 | Aglassinger | |
| D541,938 | S | 5/2007 | Kerr et al. | |
| D545,432 | S | 6/2007 | Watanabe | |
| D547,154 | S | 7/2007 | Lee | |
| 7,316,532 | B2 * | 1/2008 | Matthys-Mark | A61B 17/8057 411/3 |
| 7,318,725 | B2 | 1/2008 | Zepf | |
| D564,662 | S | 3/2008 | Moses et al. | |
| D567,943 | S | 4/2008 | Moses et al. | |
| 7,393,348 | B2 | 7/2008 | Dworschak et al. | |
| D575,395 | S | 8/2008 | Hushka | |

(56) References Cited

U.S. PATENT DOCUMENTS

| | | | |
|---|---|---|---|
| D575,401 S | 8/2008 | Hixson et al. | |
| D582,038 S | 12/2008 | Swoyer et al. | |
| 7,470,096 B2 * | 12/2008 | Morrish | B25C 3/002 206/338 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| 7,780,662 B2 | 8/2010 | Bahney | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,926,156 B2 * | 4/2011 | Jenks | B25B 7/02 269/3 |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| 8,382,810 B2 * | 2/2013 | Peterson | A61B 17/862 411/2 |
| D680,220 S | 4/2013 | Rachlin | |
| 8,591,511 B2 | 11/2013 | Romero | |
| 2006/0264922 A1 | 11/2006 | Sartor et al. | |
| 2007/0092352 A1 * | 4/2007 | Nilsen | F16B 31/021 411/5 |
| 2013/0034408 A1 * | 2/2013 | Maloney | F16B 27/00 411/445 |
| 2014/0128878 A1 * | 5/2014 | O'Neil | B25B 23/1427 606/104 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.

(56) References Cited

OTHER PUBLICATIONS

U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Heniford et al. "Initial Research and Clinical Results with an Electrothermal Bipolar Vessel Sealer" Oct. 1999. (1 page).
Michael Choti, "Abdominoperineal Resection with the LigaSure Vessel Sealing System and LigaSure Atlas 20 cm Open Instrument"; Innovations That Work, Jun. 2003. (4 pages).
Chung et al., "Clinical Experience of Sutureless Closed Hemorrhoidectomy with LigaSure" Diseases of the Colon & Rectum vol. 46, No. 1 Jan. 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000. (1 page).
Johnson et al. "Evaluation of the LigaSure Vessel Sealing System in Hemorrhoidectormy" American College of Surgeons (ACS) Clinicla Congress Poster (2000). (1 page).
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002. (4 pages).
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002. (4 pages).
Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999. (1 page).
LigaSure Vessel Sealing System, the Seal of Confidence in General, Gynecologic, Urologic, and Laparaoscopic Surgery; Sales/Product Literature; Apr. 2002. (8 pages).

Joseph Ortenberg "LigaSure System Used in Laparoscopic 1st and 2nd Stage Orchiopexy" Innovations That Work, Nov. 2002. (4 pages).
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).

(56) References Cited

OTHER PUBLICATIONS

U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 14/065,644, filed Oct. 29, 2013; inventor: Reschke.

* cited by examiner

SURGICAL INSTRUMENTS AND DEVICES AND METHODS FACILITATING THE MANUFACTURE OF THE SAME

BACKGROUND

Technical Field

The present disclosure relates to surgical instruments and, more particularly, to surgical forceps configured for treating tissue, and devices and methods facilitating the manufacture of the same.

Background of Related Art

A surgical forceps is a plier-like device which relies on mechanical action between its jaws to grasp, clamp, and constrict tissue. Energy-based surgical forceps utilize both mechanical clamping action and energy to treat, e.g., coagulate, cauterize, and/or seal, tissue.

Generally, surgical instruments, including surgical forceps, can be classified as disposable instruments, e.g., instruments that are discarded after a single use, or reusable instruments, e.g., instruments capable of being sterilized for repeated use. As can be appreciated, those instruments that are configured for single-use must be cost-efficient while still being capable of effectively performing their intended functions.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

An assembly tool provided in accordance with the present disclosure and configured for facilitating assembly of a surgical instrument includes a handle, a neck extending distally from the handle and defining a longitudinal axis, and a portion of or an entire first pivot pin engaged with the neck via a frangible connection and extending distally from the neck along the longitudinal axis. The first pivot pin is engagable with the surgical instrument as part of the assembly thereof. The frangible connection is configured to break upon application of stress thereto above a threshold, thereby separating the first pivot pin (or portion thereof) from the neck.

In an aspect of the present disclosure, the entire first pivot pin is engaged with the neck.

In another aspect of the present disclosure, a plurality of second pivot pins are aligned in end-to-end relation along the longitudinal axis and engaged with one another via frangible connections. One of the plurality of second pivot pins is engaged with the first pivot pin via a frangible connection. Each of the frangible connections is configured to break upon application of stress thereto above a threshold, thereby separating the corresponding pivot pin from the neck.

In yet another aspect of the present disclosure, the frangible connections define increasing thresholds in a distal-to-proximal direction such that a distal-most pivot pin is broken off prior to breaking of any of the other frangible connections.

In aspects of the present disclosure, the first pivot pin and each of the plurality of second pivot pins may be similar to one another, or may be include at least two different configurations.

In still another aspect of the present disclosure, a first component of the first pivot pin is engaged with the neck. The first component is configured to engage a second component to form the first pivot pin. The first and second components may be configured to engage one another via threaded engagement, friction-fitting, or in any other suitable fashion.

In still yet another aspect of the present disclosure, the threshold is configured to facilitate breaking-off of the first component from the neck after the first and second components are engaged with one another.

In an aspect of the present disclosure, the neck of the assembly tool is releasably engagable with the handle of the assembly tool.

A method of assembling a surgical instrument, or portion thereof, provided in accordance with aspects of the present disclosure includes positioning one or more components of a surgical instrument for receipt of a pivot pin, manipulating an assembly tool having the pivot pin (or a portion thereof) engaged thereon such that the pivot pin (or portion thereof) operably engages the one or more components of the surgical instrument, and manipulating the assembly tool to apply stress to a frangible connection between the assembly tool and the pivot pin (or portion thereof). The applied stress is above a threshold such that the pivot pin (or portion thereof) breaks off from the assembly tool along the frangible connection, thereby separating the pivot pin (or portion thereof) from the assembly tool.

In an aspect of the present disclosure, the entire pivot pin initially engages with the assembly tool. In such aspects, the entire pivot pin breaks off from the assembly tool along the frangible connection.

In another aspect of the present disclosure, a first part of the pivot pin engages the assembly tool. In such aspects, the method may include operably engaging a second part of the pivot pin with the one or more components of the surgical instrument, and engaging the first and second parts of the pivot pin with one another. The first and second parts of the pivot pin may be engaged with one another via threaded engagement, friction-fitting, or in any other suitable fashion.

In yet another aspect of the present disclosure, manipulation of the assembly tool applies stress to the frangible connection to break off the first part from the assembly tool along the frangible connection after the first and second parts of the pivot pin are engaged with one another.

In still another aspect of the present disclosure, manipulating the assembly tool to operably engage the pivot pin (or portion thereof) with the one or more components includes manipulating the assembly tool in at least two different directions.

In still yet another aspect of the present disclosure, positioning the one or more components of the surgical instrument for receipt of the pivot pin includes aligning apertures defined through first and second jaw members. Further, in such aspects, manipulating the assembly tool enables insertion of the pivot pin (or portion thereof) through the aligned apertures to thereby pivotably couple the first and second jaw members to one another.

A method of assembling one or more surgical instruments, in accordance with aspects of the present disclosure, includes positioning one or more first components of a first surgical instrument for receipt of a first pivot pin, manipulating an assembly tool having a plurality of pivot pins engaged thereon such that the first pivot pin of the plurality of pivot pins operably engages the first component(s), manipulating the assembly tool to apply stress to a first frangible connection engaging the first pivot pin with the assembly tool such that the first pivot pin breaks off from the assembly tool, positioning one or more second components of the first surgical instrument or of a second surgical instrument for receipt of a second pivot pin, manipulating the assembly tool such that the second pivot pin of the plurality of pivot pins operably engages the second component(s), and manipulating the assembly tool to apply stress to a second frangible connection engaging the second pivot pin with the assembly tool such that the second pivot pin breaks off from the assembly tool.

In aspects, the threshold for breaking the second frangible connection is greater than the threshold for breaking the first frangible connection to facilitate breaking-off of the first pivot pin before breaking-off of the second pivot pin.

BRIEF DESCRIPTION OF THE DRAWINGS

Various aspects and features of the present disclosure described herein with reference to the drawings wherein.

DETAILED DESCRIPTION

Figure 1A:
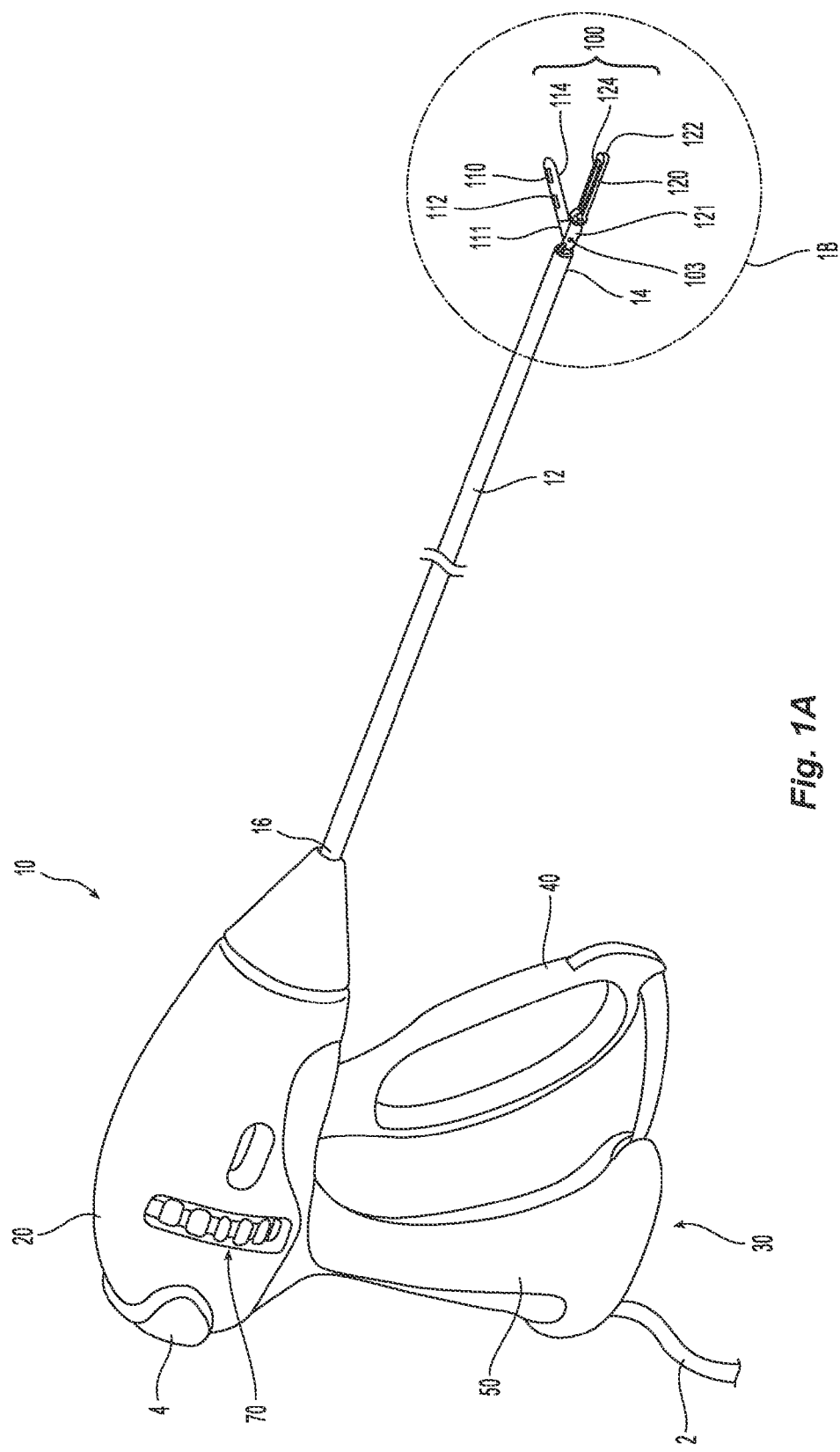
FIG. 1A is a perspective view of an endoscopic surgical forceps.
Figure 2:
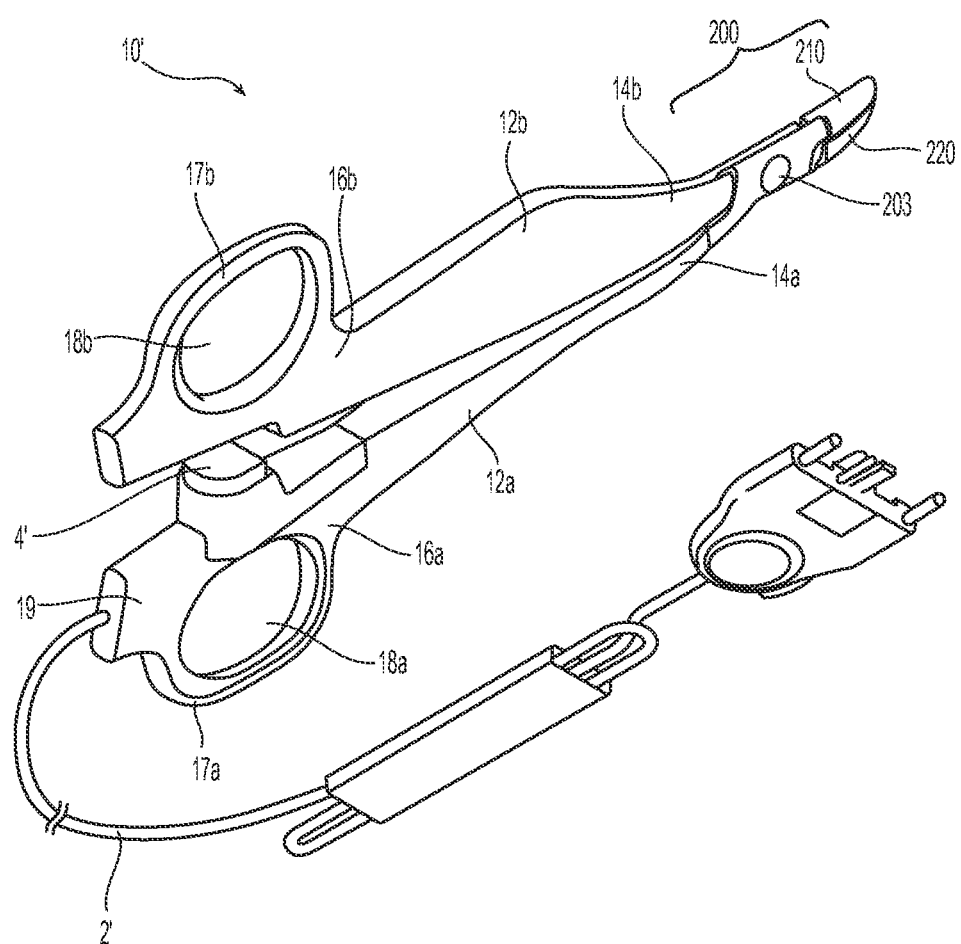
FIG. 2 is a perspective view of an open surgical forceps.

Turning to FIGS. 1A and 2, FIG. 1A depicts a endoscopic surgical forceps 10 and FIG. 2 depicts a hemostat-style forceps 10'. The aspects and features of the present disclosure are applicable to forceps 10, forceps 10', or any other suitable surgical instrument. Obviously, different electrical and mechanical connections and considerations apply to each particular type of instrument; however, the aspects and features of the present disclosure remain generally consistent regardless of the particular instrument used.

Referring to FIG. 1A, forceps 10 generally includes a housing 20, a handle assembly 30, a rotating assembly 70, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-treating surfaces 114, 124 (FIG. 1B) of jaw members 110, 120, respectively. However, energy may be supplied to respective tissue-treating surfaces 114, 124 (FIG. 1B) of jaw members 110, 120 in any other suitable fashion, e.g., via conductive structural components of forceps 10, brush-contacts, etc. Activation switch 4 is coupled between tissue-treating surfaces 114, 124 (FIG. 1B) of jaw members 110, 120, respectively, and the source of energy for enabling the selective supply of energy to jaw members 110, 120 for treating tissue grasped therebetween. Rotating assembly 70 is rotatable in either direction to rotate end effector assembly 100 relative to housing 20.

Handle assembly 30 includes a fixed handle 50 and a movable handle 40. Fixed handle 50 is integrally associated with housing 20 and movable handle 40 is movable relative to fixed handle 50. More specifically, movable handle 40 is pivotably coupled to housing 20 within housing 20 via a pivot pin (not shown) and operably coupled to a drive assembly (not shown) disposed within housing 20 such that movable handle 40 and the drive assembly (not shown), together, mechanically cooperate to impart movement of one or both of jaw members 110, 120 about a pivot pin 103 between a spaced-apart position and an approximated position to grasp tissue between jaw members 110, 120. As shown in FIG. 1A, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120.

Figure 1B:
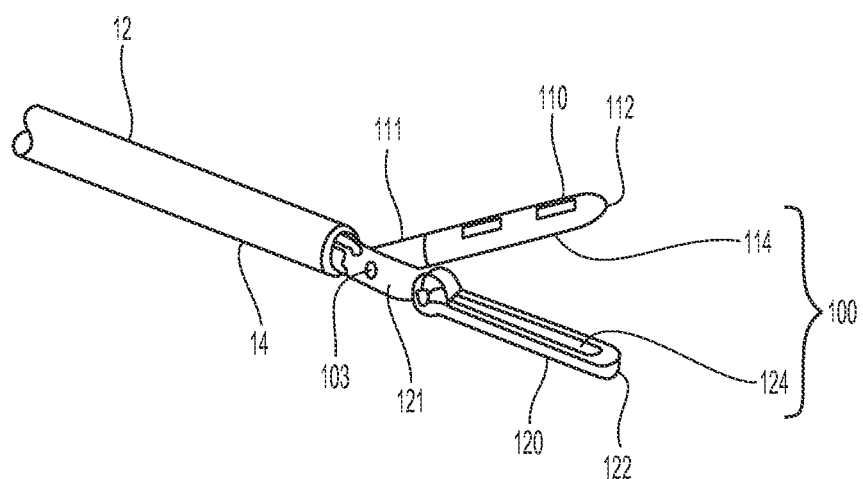
FIG. 1B is an enlarged, perspective view of the area of detail indicated as "1B" in FIG. 1A, illustrating the end effector assembly of the forceps of FIG. 1A.

Referring to FIG. 2, forceps 10' is shown including two elongated shaft members 12a, 12b, each having a proximal end 16a, 16b, and a distal end 14a, 14b, respectively. Forceps 10' further includes an end effector assembly 200 similar to end effector assembly 100 (FIGS. 1A and 1B). More specifically, end effector assembly 200 includes first and second jaw members 210, 220 attached to respective distal ends 14a, 14b of shaft members 12a, 12b and pivotably coupled to one another about a pivot pin 203. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of the shaft members 12a, 12b relative to one another to, in turn, pivot jaw members 210, 220 between a spaced-apart position and an approximated position for grasping tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 2' to forceps 10' such that the user may selectively supply energy to jaw members 210, 220 for treating tissue grasped therebetween. More specifically, an activation switch 4' is positioned to initiate the supply of energy to jaw members 210, 220 upon sufficient approximation of shaft members 12a, 12b.

With reference to FIG. 1B, end effector assembly 100 of forceps 10 (FIG. 1A) is shown, keeping in mind that end effector assembly 200 includes similar features. Each jaw member 110, 120 of end effector assembly 100 includes a proximal flange 111, 121 and a distal jaw body 112, 122 upon which respective tissue-treating surfaces 114, 124 are defined. Proximal flanges 111, 121 are pivotably coupled to one another about a pivot pin 103. One or both of proximal flanges 111, 121 is pivotably coupled to shaft 12 via pivot pin 103 and operably coupled to the drive assembly (not shown), e.g., via a pivot pin (not shown), such that movable handle 40 (FIG. 1A) is operable to pivot jaw members 110, 120 relative to one another between the spaced-apart and approximated positions.

Figure 3A:
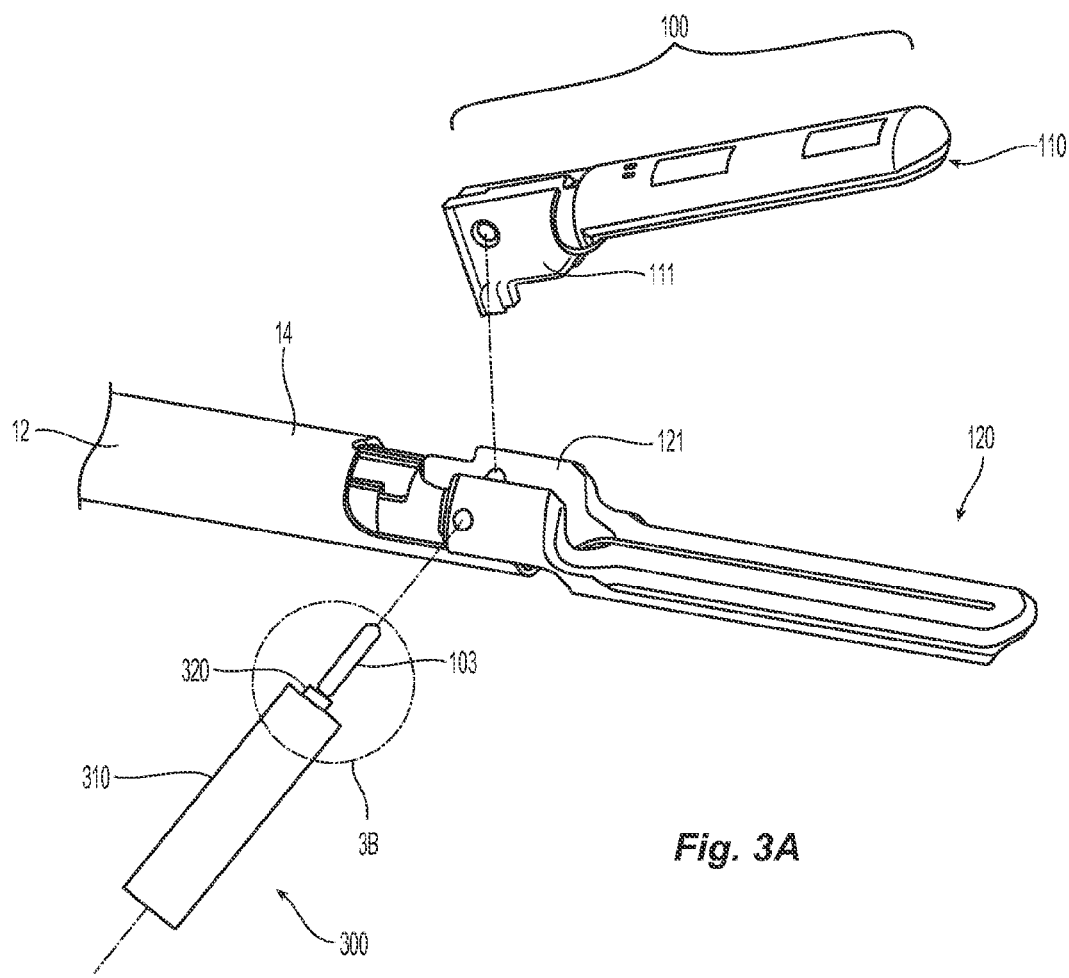
FIG. 3A is an exploded, perspective view of the end effector assembly of FIG. 1B with an assembly tool provided in accordance with the present disclosure that is utilized to facilitate assembly of the end effector assembly.
Figure 3B:
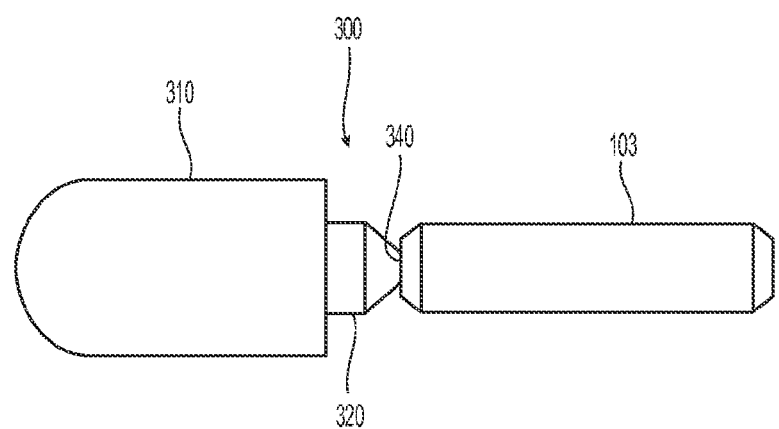
FIG. 3B is an enlarged, side view of the area of detail indicated as "3B" in FIG. 3A.

Turning now to FIGS. 3A-3B, an assembly tool 300 utilized to facilitate the assembly of forceps 10 (FIG. 1A) is shown configured for use in installing pivot pin 103 to pivotably couple jaw member 110 with jaw member 120 and shaft 12. Assembly tool 300 may alternatively or additionally be configured for use in installing any other pivot pin associated with forceps 10 (FIG. 1A), e.g., the pivot pin (not shown) coupling movable handle 40 with housing 20 (FIG. 1A), the pivot pin (not shown) operably coupling the drive assembly (not shown) with end effector assembly 100, etc., or for installing one or more pivot pins of any other suitable surgical instrument or component thereof.

Assembly tool 300 includes a handle 310 configured to be grasped by a user, a neck 320 extending distally from handle 310, and pivot pin 103 engaged with and extending distally from neck 320. Pivot pin 103 may be monolithically formed with neck 320 or otherwise engaged therewith to define a frangible section 340 between pivot pin 103 and neck 320 that is configured to break under a threshold amount of stress, thereby separating pivot pin 103 from neck 320. Frangible section 340 defines a lower breaking-point as compared to pivot pin 103, handle 310, neck 320, and the connection between handle 310 and neck 320 such that frangible section 340 breaks, thereby separating pivot pin 103 from neck 320, prior to breaking of any of the other components or portions of assembly tool 300. It is contemplated that neck 320 may be releasably coupled with handle 310 such that, after pivot pin 103 is broken off from neck 320, a new neck 320 having another pivot pin attached thereto maybe loaded onto handle 310 for further use, e.g., for insertion of another pin associated with forceps 10 (FIG. 1A).

Figure 4A:
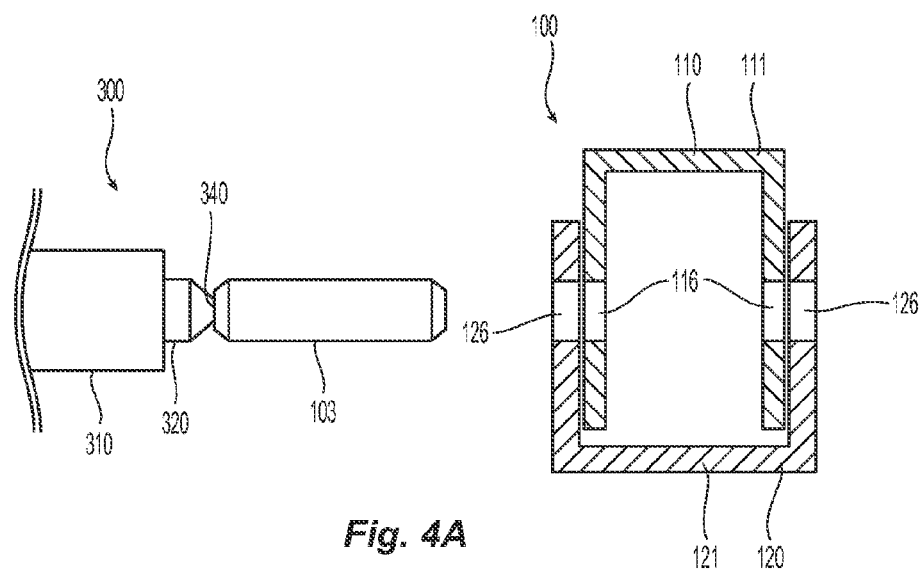
FIGS. 4A-4C are transverse, cross-sectional views illustrating assembly of the end effector assembly of FIG. 1A in accordance with aspects of the present disclosure, using the assembly tool of FIG. 3A.
Figure 4B:
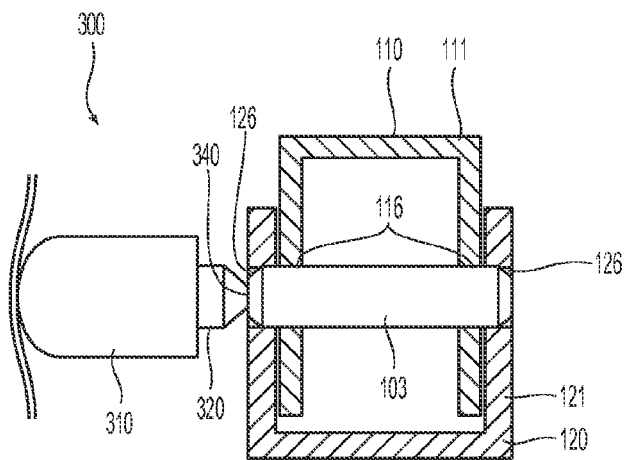
Figure 4C:
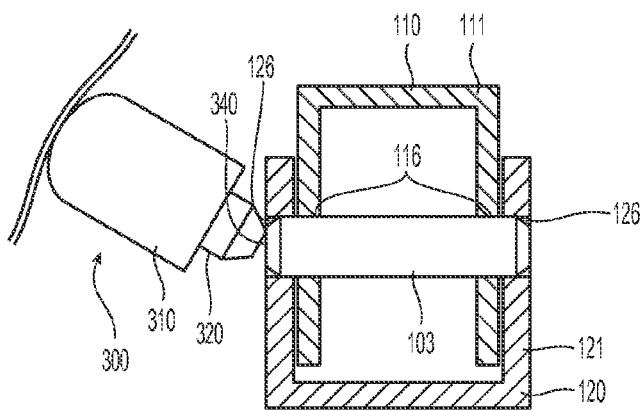

Referring to FIGS. 4A-4C, the use of assembly tool 300 for facilitating the assembly of forceps 10 (FIG. 1A), e.g., the pivotable coupling of jaw member 110 with jaw member 120 and shaft 12 (FIG. 1A) is detailed. Initially, with reference to FIG. 4A, proximal flanges 111, 121 of jaw members 110, 120, respectively, are aligned with one another such that the pairs of apertures 116, 126 defined through respective proximal flanges 111, 121 are aligned with one another. Thereafter, with additional reference to FIG. 4B, handle 310 of assembly tool 300 is manipulated such that pivot pin 103 is inserted through each set of aligned apertures 116, 126 to pivotably couple proximal flanges 111, 121 to one another.

Referring also to FIG. 4C, once pivot pin 103 is inserted through each set of aligned apertures 116, 126 sufficiently so as to pivotably couple proximal flanges 111, 121 to one another, handle 310 is manipulated off-axis relative to pivot pin 103 and aligned apertures 116, 126 so as to impart stress to the frangible section 340 defined between pivot pin 103 and neck 320 (as a result of pivot pin 103 being captured within apertures 116, 126 and, thus, unable to move in accordance with the movement of handle 310). Upon sufficient off-axis manipulation of handle 310 so as to impart the threshold amount of stress to frangible section 340, pivot pin 103 is broken-off from neck 320, leaving pivot pin 103 in position operably engaging proximal flanges 111, 121 with one another. Although this may be sufficient to secure pivot pin 103 in position, pivot pin 103 may further be secured in position using end caps, adhesives, welding, any of the configurations detailed below, or other suitable mechanisms or methods, to inhibit dislodging of pivot pin 103 from apertures 116, 126.

Figure 5A:
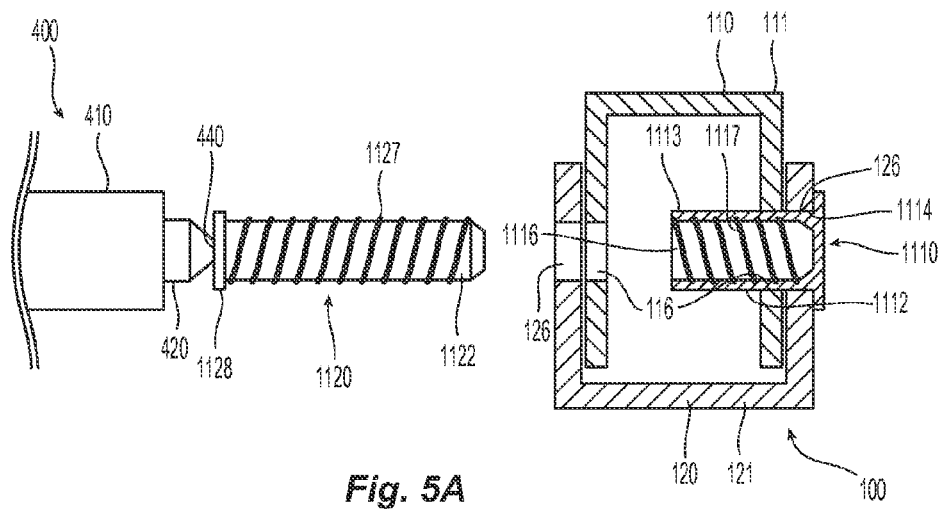
FIGS. 5A-5C are transverse, cross-sectional views illustrating assembly of the end effector assembly of FIG. 1A in accordance with aspects of the present disclosure, using an assembly tool similar to the assembly tool of FIG. 3A.
Figure 5B:
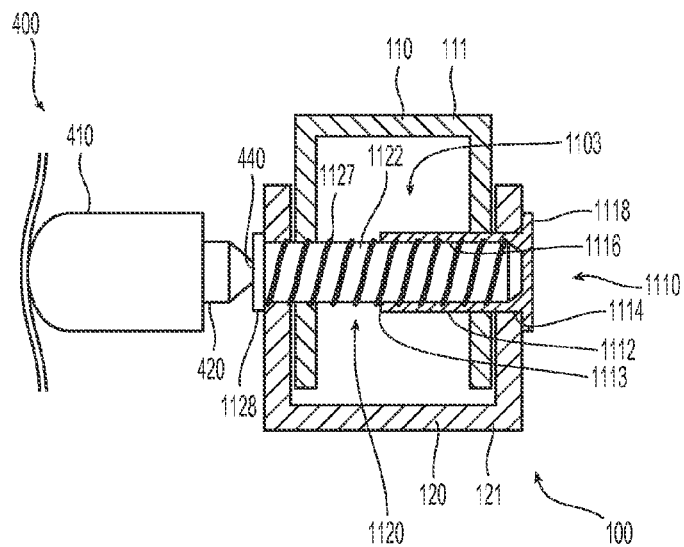
Figure 5C:
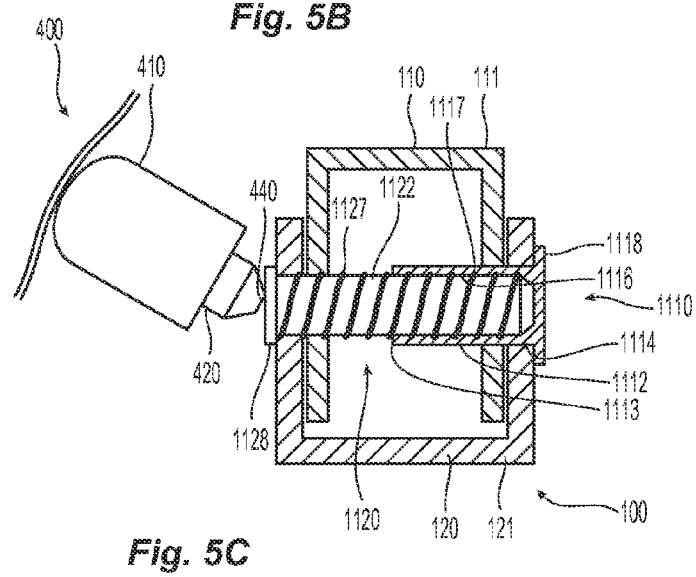

Turning now to FIGS. 5A-5C, another assembly tool 400 provided in accordance with the present disclosure for facilitating the assembly of forceps 10 (FIG. 1A) is shown configured for use in installing a two-part pivot pin 1103 to pivotably couple jaw member 110 with jaw member 120 and shaft 12, although assembly tool 400 may also be configured for use in installing a pivot pin of any other suitable surgical instrument or component thereof.

Two-part pivot pin 1103 includes a female component 1110 and a male component 1120 configured to engage female component 1110. Female component 1110 includes a body 1112 defining an open end 1113 and a closed end 1114, and a collar 1118 defined at closed end 1114 of body 1112. An interior lumen 1116 extends inwardly from open end 1113 of body 1112. Threading 1117 is disposed on the interior surface of body 1112 defined by interior lumen 1116. Male component 1120 includes a body 1122 and includes a collar 1128 defined at an end thereof. Body 1122 of male component 1120 defines a diameter equal to or slightly less than that of lumen 1116 of female component 1110 and defines complementary threading 1127 on the exterior thereof to enable threading engagement of male component 1120 within female component 1110. However, nonthreaded engagement, e.g., friction-fitting, is also contemplated.

Assembly tool 400 is similar to assembly tool 300 (FIGS. 3A and 3B) and includes a handle 410, a neck 420 extending distally from handle 410, and male component 1120 of two-part pivot pin 1103 engaged with and extending distally form neck 420. More specifically, collar 1128 of male component 1120 is monolithically formed with neck 420 or otherwise engaged therewith to define a frangible section 440 between male component 1120 of pivot pin 1103 and neck 420. Frangible section 440 defines a lower breakingpoint as compared to the threadings 1117, 1127 of female and male components 1110, 1120, respectively, of two-part pivot pin 1103, such that frangible section 440 breaks, thereby separating pivot pin 1103 from neck 420, prior to breaking the threaded engagement between female and male components 1110, 1120, respectively, of two-part pivot pin 1103. Assembly tool 400 may further include any of the aspects and features of assembly tool 300 (FIGS. 3A and 3B), detailed above, and vice versa.

Continuing with referring to FIGS. 5A-5C, the use of assembly tool 400 for facilitating the assembly of forceps 10 (FIG. 1A), e.g., the pivotable coupling of jaw member 110 with jaw member 120 and shaft 12 (FIG. 1A), is detailed. Initially, with reference to FIG. 5A, proximal flanges 111, 121 of jaw members 110, 120, respectively, are aligned with one another such that the pairs of apertures 116, 126 defined through respective proximal flanges 111, 121 are aligned with one another. Female component 1110 of two-part pivot pin 1103, led by open end 1113 of body 1112, is then inserted through one set of aligned apertures 116, 126.

With additional reference to FIG. 5B, handle 410 of assembly tool 400 is manipulated such that male component 1120 of two-part pivot pin 1103 is inserted through the other set of aligned apertures 116, 126 and into position adjacent female component 1110. Thereafter, handle 410 is rotated about its longitudinal axis and relative to female component 1110 of two-part pivot pin 1103 so as to advance body 1122 of male component 1120 into lumen 1116 of body 1112 of female component 1110 in threaded engagement therewith.

Referring also to FIG. 5C, body 1122 of male component 1120 is fully engaged within lumen 1116 of body 1112 of female component 1110 such that two-part pivot pin 1103 pivotably couples proximal flanges 111, 121 to one another and is retained in position via collars 1118, 1128 of female and male components 1110, 1120, respectively, on either side of flanges 111, 121. At this point, assembly tool 400 may be broken off from two-part pivot pin 1103 and removed. In order to break-off assembly tool 400 from two-part pivot pin 1103, handle 410 may be further rotated about its longitudinal axis, resulting in stress being imparted to frangible section 440 since male component 1120 is fully engaged within female component 1110 and, thus, cannot be rotated with the rotation of handle 410. As noted above, as the frangible section 440 has a lower break-off point relative to surrounding components and engagements therebetween, male component 1120 is broken-off from neck 420 prior to breaking any other components or engagements. In embodiments where non-threaded engagement, e.g., friction-fitting, is provided, breaking-off of assembly tool 400 from pivot pin 1103 may be accomplished similarly as detailed above with respect to assembly tool 300 (FIGS. 4A-4C). It is also contemplated that two-part pivot pin 1103 (with or without threading) may be operably engaged with jaw members 110, 120 without the use of assembly tool 400, e.g., via any other suitable mechanism.

Figure 6:
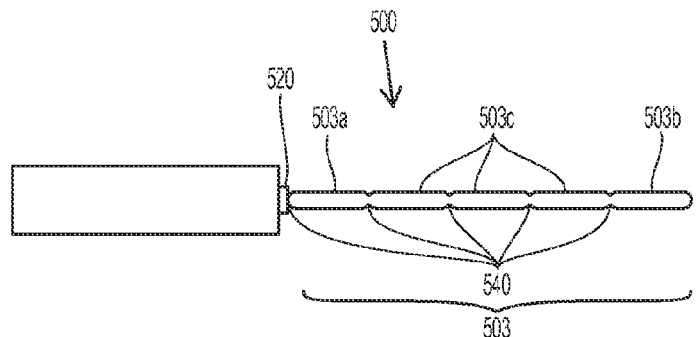
FIG. 6 is a side view of another assembly tool provided in accordance with aspects of the present disclosure.

Turning to FIG. 6, another assembly tool 500 provided in accordance with the present disclosure for facilitating the assembly of forceps 10 (FIG. 1A), or any other suitable surgical instrument, is shown. Assembly tool 500 may be similar to assembly tools 300, 400 (FIGS. 4A-4C and 5A-5C, respectively) except that, rather than providing a single pivot pin coupled thereto, assembly tool 500 includes a series of pivot pins 503 engaged therewith. Pivot pins 503 are arranged end-to-end with one another along a longitudinal axis of assembly tool 500. A proximal-most pivot pin 503a is engaged or formed with neck 520 of assembly tool 500, while a distal-most pivot pin 503b defines a free distal end. A plurality of intermediate pivot pins 503c are interdisposed between proximal-most pivot pin 503a and distal-most pivot pin 503b. The pivot pins 503 may be different from one another and/or configured for engaging different portions of forceps 10 (FIG. 1A) or other suitable surgical instrument, or may be similar to one another and interchangeably usable for engaging one or more portions of forceps 10 (FIG. 1A) or for use in assembling multiple forceps 10 (FIG. 1A). Where different or specialized pivot pins 503 are provided, the pivot pins 503 may be arranged in the order in which they are to be needed during assembly.

A frangible portion 540 is defined between proximal-most pivot pin 503a and neck 520, between proximal-most pivot pin 503a and the proximal-most intermediate pivot pin 503c, between each of the intermediate pivot pins 503c, and between the distal-most intermediate pivot pin 503c and distal-most pivot pin 503b. Similarly as detailed above, frangible portions 540 enable successive breaking off of pivot pins 503 from assembly tool 500, while the more-proximal pivot pins 503 remain engaged with assembly tool 500. Frangible portions 540 may define increasing breaking thresholds in the distal-to-proximal direction such that only the distal-most of the pivot pins 503 is broken off, while the other pivot pins 503 remain engaged. Alternatively, assembly tool 500 may include features to inhibit additional pivot pins 503, other than the distal-most of the pivot pins 503, to be broken off.

Figure 7A:
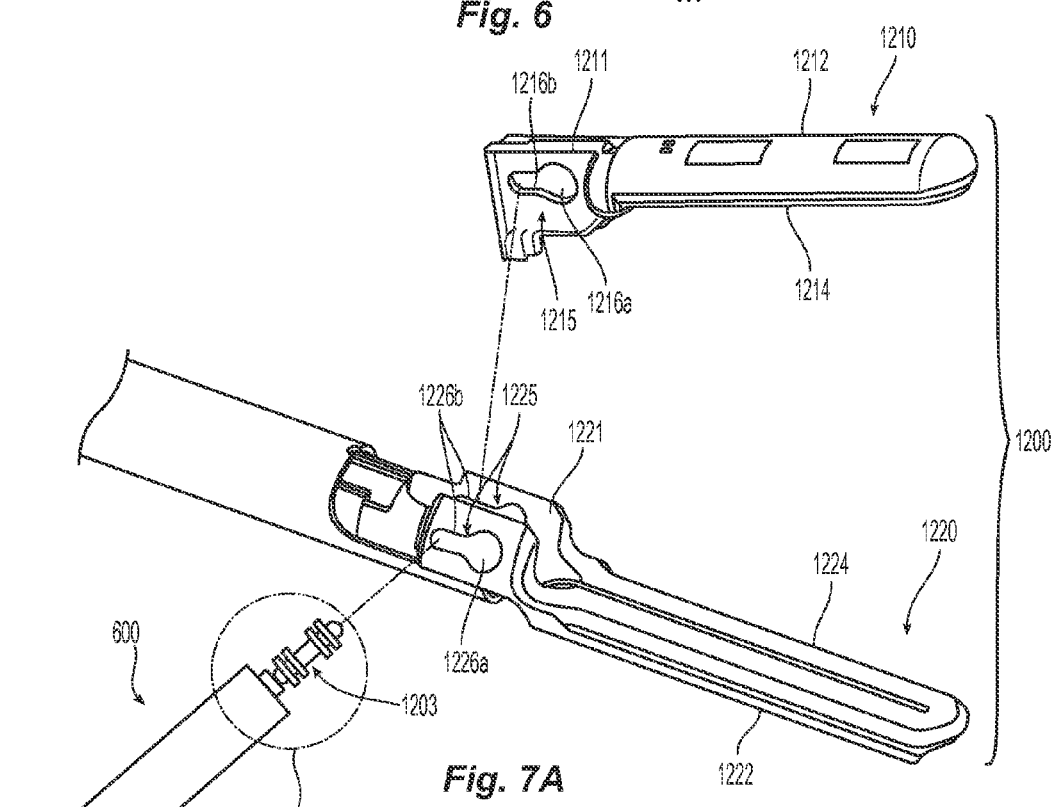
FIG. 7A is an exploded, perspective view of another end effector assembly provided in accordance with the present disclosure, wherein another assembly tool provided in accordance with the present disclosure is utilized to facilitate assembly of the end effector assembly.
Figure 7B:
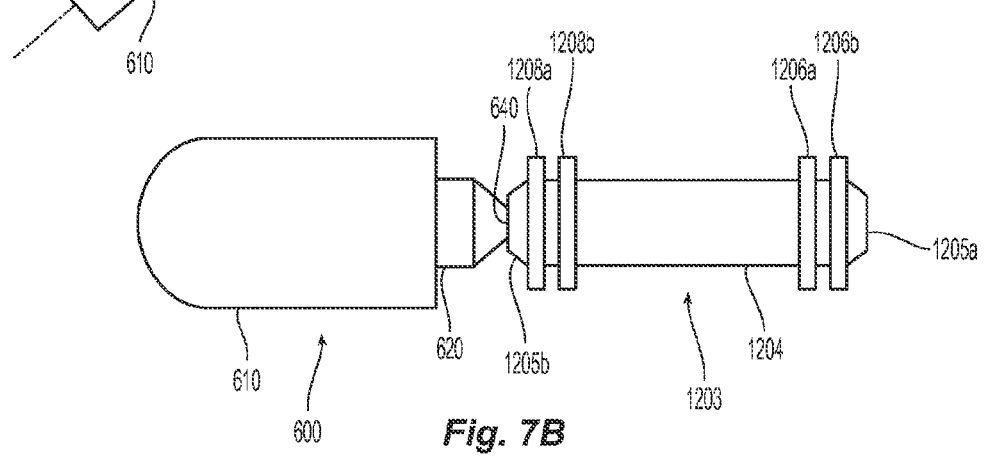
FIG. 7B is an enlarged, side view of the area of detail indicated as "7B" in FIG. 7A.

With reference to FIGS. 7A and 7B, another end effector assembly 1200 and assembly tool 600 for use therewith provided in accordance with the present disclosure are detailed. Although described together, it is contemplated that end effector assembly 1200 be assembled without use of assembly tool 600. End effector assembly 1200 is similar to end effector assembly 100 (FIG. 1B) and includes first and second jaw members 1210, 1220, each including a proximal flange 1211, 1221 and a distal jaw body 1212, 1222 upon which respective tissue-treating surfaces 1214, 1224 are defined. Proximal flanges 1211, 1221 each define a pair of openings 1215, 1225 for receipt of a pivot pin 1203 for pivotably coupling jaw members 1210, 1220 to one another. Each opening 1215, 1225 defines an enlarged-area portion 1216a, 1226a and reduced-area portion 1216b, 1226b in communication with and extending proximally from the respective enlarged-area portion 1216a, 1226a.

Pivot pin 1203 is engaged with neck 620 of assembly tool 600, similarly as detailed above with respect to assembly tool 300 and pivot pin 103 (FIGS. 4A-4C). Pivot pin 1203 defines a generally cylindrical body 1204 having first and second ends 1205a, 1205b. A pair of spaced-apart annular ribs 1206a, 1206b and 1208a, 1208b is monolithically formed with or engaged about pivot pin 1203 towards each of the first and second ends 1205a, 1205b thereof. Annular ribs 1206a, 1206b and 1208a, 1208b define diameters greater than that of reduced-area portions 1216b, 1226b of openings 1215, 1225 of proximal flanges 1211, 1221 of jaw members 1210, 1220 but less than that of enlarged-area portions 1216a, 1226a of openings 1215, 1225 of proximal flanges 1211, 1221 of jaw members 1210, 1220.

Continuing with reference to FIGS. 7A and 7B, in order to assemble end effector assembly 1200 using assembly tool 600, proximal flanges 1211, 1221 of jaw members 1210, 1220, respectively, are first aligned with one another such that openings 1215, 1225 are aligned with one another. Thereafter, handle 610 of assembly tool 600 is manipulated such that pivot pin 1203 is inserted through enlarged-area portions 1216a, 1226a of openings 1215, 1225. More specifically, pivot pin 1203 is positioned such that a portion of each of proximal flanges 1211, 1221 is disposed between each pair of annular ribs 1206a, 1206b and 1208a, 1208b.

Once pivot pin 1203 is positioned such that a portion of each of proximal flanges 1211, 1221 is disposed between each pair of annular ribs 1206a, 1206b and 1208a, 1208b, handle 610 may further be manipulated so as to translate pivot pin 1203 proximally from the enlarged-area portions 1216a, 1226a of openings 1215, 1225 to the reduced-area portions 1216b, 1226b of openings 1215, 1225. In this position, lateral movement of pivot pin 1203 is inhibited due to the portions of proximal flanges 1211, 1221 being disposed between each pair of annular ribs 1206a, 1206b and 1208a, 1208b. Pivot pin 1203 may be inhibited from returning distally once this position has been achieved directly, e.g., via closing or blocking enlarged-area portions 1216a, 1226a of openings 1215, 1225, or indirectly, e.g., via interference from other components of end effector assembly 1200 upon full assembly of end effector assembly 1200.

With pivot pin 1203 in position as detailed above, handle 610 may be manipulated off-axis relative to pivot pin 1203 and openings 1215, 1225 so as to impart stress to the frangible section 640 defined between pivot pin 1203 and neck 620. Upon sufficient off-axis manipulation of handle 610, pivot pin 1203 is broken-off from neck 620, leaving pivot pin 1203 in position operably engaging jaw members 1210, 1220 with one another.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An assembly tool for facilitating assembly of a surgical instrument, comprising:
    a handle;
    a first neck releasably engagable with the handle and extending distally from the handle; and
    a pivot pin assembly including:
        an elongated proximal component having a proximal portion engaged with the first neck via a frangible connection, the elongated proximal component extending distally from the first neck; and
        an elongated distal component configured to engage the elongated proximal component, the elongated distal component having a closed distal end from which a distal collar extends radially outward, the pivot pin assembly engagable with the surgical instrument such that at least one jaw member of a pair of jaw members of the surgical instrument is movable relative to the other jaw member about the pivot pin assembly, the frangible connection configured to break upon application of stress thereto above a threshold, thereby separating the pivot pin assembly from the first neck.

2. The assembly tool according to claim 1, wherein the proximal portion of the elongated proximal component is coupled to the first neck via a proximal collar that extends radially outward from the elongated proximal component.

3. The assembly tool according to claim 1, wherein the proximal and distal components are configured to engage one another via threaded engagement or friction-fitting.

4. The assembly tool according to claim 1, wherein the threshold is configured to facilitate breaking-off of the elongated proximal component from the first neck after the elongated proximal and distal components are engaged with one another.

* * * * *